(12) United States Patent
Peters (10) Patent No.: US 8,241,650 B2
(45) Date of Patent: Aug. 14, 2012

(54) DEVICE, METHOD, AND USE FOR TREATMENT OF NEUROPATHY INVOLVING NITRIC OXIDE

(75) Inventor: Tor Peters, Helsingborg (SE)

(73) Assignee: Nolabs AB, Helsingborg (SE)

(*) Notice: Subject to any disclaimer, the term of this patent is extended or adjusted under 35 U.S.C. 154(b) by 1228 days.

(21) Appl. No.: 11/891,678

(22) Filed: Aug. 10, 2007

(65) Prior Publication Data

US 2008/0069848 A1     Mar. 20, 2008

Related U.S. Application Data

(63) Continuation of application No. PCT/EP2006/050891, filed on Feb. 13, 2006.

(60) Provisional application No. 60/652,760, filed on Feb. 14, 2005, provisional application No. 60/711,006, filed on Aug. 24, 2005.

(30) Foreign Application Priority Data

Feb. 11, 2005   (EP) .................................... 05002935
Aug. 23, 2005   (EP) .................................... 05018269

(51) Int. Cl.
  *A61K 33/00*   (2006.01)
  *A61K 9/00*   (2006.01)
  *A61P 25/02*   (2006.01)

(52) U.S. Cl. ......... 424/402; 424/400; 424/484; 424/718

(58) Field of Classification Search .......................... None
See application file for complete search history.

(56) References Cited

U.S. PATENT DOCUMENTS

| 3,754,368 | A | * | 8/1973 | Moore et al. ..................... 53/431 |
| 4,182,827 | A | * | 1/1980 | Jones et al. ..................... 528/60 |
| 5,519,020 | A |   | 5/1996 | Smith et al. |
| 5,691,423 | A |   | 11/1997 | Smith et al. |
| 5,770,645 | A |   | 6/1998 | Stamler et al. |
| 5,814,656 | A | * | 9/1998 | Saavedra et al. .............. 514/426 |

(Continued)

FOREIGN PATENT DOCUMENTS

EP    1300424 A1    4/2003

(Continued)

OTHER PUBLICATIONS

Bohl Masters et al., *Effects of nitric oxide releasing poly(vinyl alcohol) hydrogel dressings on dermal wound healing in diabetic mice*. Wound Repair and Regeneration, 2002, 286-294, 10(5), Blackwell Publishing Ltd., Malden, Massachusetts.

(Continued)

*Primary Examiner* — Robert A Wax
*Assistant Examiner* — William Craigo
(74) *Attorney, Agent, or Firm* — Knobbe Martens Olson & Bear LLP (57) ABSTRACT

A device is provided that allows for target treatment of neuropathy, such as diabetic peripheral neuropathy, or neuropathy and ulcers resulting from said neuropathy. The device comprises a nitric oxide (NO) eluting polymer arranged to contact a treatment area, such that a therapeutic dose of nitric oxide is eluted from said nitric oxide eluting polymer to said area. The nitric oxide (NO) eluting polymer is integrated with a carrier material, such that the carrier material, in use, regulates and controls the elution of the therapeutic dosage of nitric oxide (NO). Furthermore, a corresponding manufacturing method for the device is disclosed.

27 Claims, 4 Drawing Sheets

U.S. PATENT DOCUMENTS

| | | | |
|---|---|---|---|
| 5,814,666 A | 9/1998 | Green et al. | |
| 5,958,427 A | 9/1999 | Salzman et al. | |
| 6,110,453 A | 8/2000 | Keefer et al. | |
| 6,382,526 B1 | 5/2002 | Reneker et al. | |
| 6,520,425 B1 | 2/2003 | Reneker | |
| 6,695,992 B2 | 2/2004 | Reneker | |
| 6,737,447 B1* | 5/2004 | Smith et al. | 523/105 |
| 6,818,018 B1* | 11/2004 | Sawhney | 623/11.11 |
| 6,861,064 B1* | 3/2005 | Laakso et al. | 424/408 |
| 2002/0012816 A1 | 1/2002 | Shimizu et al. | |
| 2002/0082221 A1 | 6/2002 | Herrmann et al. | |
| 2002/0094985 A1* | 7/2002 | Herrmann et al. | 514/245 |
| 2002/0136750 A1 | 9/2002 | Benjamin et al. | |
| 2003/0235605 A1* | 12/2003 | Lelah et al. | 424/443 |
| 2004/0009238 A1* | 1/2004 | Miller et al. | 424/718 |
| 2004/0043068 A1 | 3/2004 | Tedeschi et al. | |
| 2004/0068005 A1 | 4/2004 | Szilvassy et al. | |
| 2004/0171589 A1 | 9/2004 | Herrmann et al. | |
| 2004/0265244 A1 | 12/2004 | Rosen | |

FOREIGN PATENT DOCUMENTS

| | | | |
|---|---|---|---|
| GB | 2354441 A | 3/2001 | |
| WO | WO 00/49993 A | 8/2000 | |
| WO | WO 01/26702 A2 | 4/2001 | |
| WO | WO 01/85013 A2 | 11/2001 | |
| WO | WO 03/078437 A1 | 9/2003 | |
| WO | WO 03/086282 A2 | 10/2003 | |
| WO | WO 03/092763 A1 | 11/2003 | |
| WO | WO 2004/012659 A2 | 2/2004 | |
| WO | WO 2004/012874 A1 | 2/2004 | |
| WO | WO 2005/003032 A1 | 1/2005 | |
| WO | WO 2005/037339 A1 | 4/2005 | |
| WO | WO 2005/046661 A2 | 5/2005 | |

OTHER PUBLICATIONS

Puffer et at, *Incorporation of Nitric Oxide-Releasing Crosslinked Polyethyleneimine Microspheres Into Vascular Grafts*, Journal of Biomedical Materials Research, 1997, 182-189, 37(2), John Wiley & Sons Inc., New York, NY.

Smith et al., *Transdermal delivery of nitric oxide from diazeniumdiolate*, Journal of Controlled Release, 1998, 153-159, 51(2-3), Elsevier Science Publishers, Amsterdam, NL.

* cited by examiner

DEVICE, METHOD, AND USE FOR TREATMENT OF NEUROPATHY INVOLVING NITRIC OXIDE

RELATED APPLICATIONS

This application is a continuation of PCT/EP2006/050891, filed Feb. 13, 2006, which claims priority to European Patent Application No. 05002935.4, filed Feb. 11, 2005; U.S. Provisional Application No. 60/652,760, filed Feb. 14, 2005; European Patent Application No. 05018269.0, filed Aug. 23, 2005; and U.S. Provisional Application No. 60/711,006, filed Aug. 24, 2005. The entire contents of these applications is incorporated herein by reference.

BACKGROUND OF THE INVENTION

1. Field of the Invention

This invention pertains in general to the field of treatment of neuropathy, such as diabetic peripheral neuropathy, vaso-constrictive disorders, macro-angiopathy and slow healing wounds as consequence of diabetic neuropathy and impaired blood circulation due to diabetic disease or obstructed blood flow caused by other disease. More particularly the invention relates to a device for treatment of at least some of said disorders, and a process for manufacturing of said device, involving the use of nitric oxide (NO).

2. Description of the Related Art

Diabetes is a disorder that affects millions of people around the world. This disease results in increased risk for neuropathy and macro-angiopathy. Reasons for diabetic neuropathy may be varying levels of insulin or blood sugar respectively, and high blood sugar. Diabetic neuropathy, or nerve damage, resulting from chronically high blood sugars, can be one of the most frustrating and debilitating complications of diabetes, because of the pain, discomfort and disability it can cause, and because available treatments are not uniformly successful.

Diabetic neuropathy may be divided into the three main types of neuropathy; sensory neuropathy, autonomic neuropathy, and motor neuropathy. Sensory neuropathy leads to pain, numbness, tingling in the extremities, and even the inability to feel heat, cold, pain or any other sensation in the affected areas. Autonomic neuropathy leads to impotence (in men), bladder neuropathy, diabetic diarrhea, or swollen stomach. Motor neuropathy leads to muscle weakness.

As a direct and indirect consequence of diabetic neuropathy the person suffering from this disorder may develop ulcers, so-called diabetic ulcers. These diabetic ulcers may develop as a result of small traumas on the body. Since the diabetic person, suffering from diabetic neuropathy, has a reduced, and some times even non-existent, ability to feel, these ulcers may develop very rapidly. Other factors that severely affect this matter are the reduced ability to heal and the reduced circulation in the affected area, which accompanies diabetic neuropathy. The reduced circulation in the affected area is a consequence of macro-angiopathy. Macro-angiopathy is a condition in which the blood vessels are enlarged and the arteries are hardened. These ulcers often result in amputation of the affected extremity. Macro-angiopathy is closely related to Peripheral Artery Obstructive Disease, and will therefore here on after be treated as the same.

Other malfunctions arising from diabetic neuropathy are vaso-constrictive disorders, such as Raynouds, or Reyes syndrome.

Up to this point in time, there are no good cures or treatment of neuropathy. Some medications, such as acetaminophen, aspirin, ibuprofen, amitriptyline, desipramine, and capsaicin, are on the market to liberate the diabetic person from pain, but these medicaments do not deal with the malfunction itself, only with the symptoms, and sometimes develop resistance against the active pharmaceutical substance in the medication. The person suffering from said disorders is instructed to apply these medicaments in form of creams and peroral compositions regularly during the day, rather than waiting for the pain to become severe. This is an all day process, which is very frustrating for the person suffering from said disorders. It is believed, in some circumstances, that these creams and compositions block pain signals, although they do not work for everyone. Occasionally, these creams and compositions may even worsen the pain or cause other adverse effects, such as eye or skin irritation. In the late 1980s and early 1990s aldose reductase inhibitors were introduced. Unfortunately, to date none of these drugs has proven to be sufficiently effective and adverse side effects have been a concern. Instead, the best advice the person suffering from said disorder can get, is to control and regulate his/her way of living, such as keeping blood sugar levels as close to normal as possible, exercise regularly, and take care of their health and weight.

It is known that nitric oxide (NO) provides an alternative to conventional therapies, such as antibiotics. Nitric oxide is a highly reactive molecule that is involved in many cell functions. In fact, nitric oxide plays a crucial role in the immune system and is utilized as an effector molecule by macrophages to protect itself against a number of pathogens, such as fungi, viruses, bacteria etc., and general microbial invasion. This improvement of healing is partly caused by NO inhibiting the activation or aggregation of blood platelets, and also by NO causing a reduction of inflammatory processes at the site of an implant.

NO is also known to have an anti-pathogenic, especially an anti-viral, effect, and furthermore NO has an anti-cancerous effect, as it is cytotoxic and cytostatic in therapeutic concentrations, i.e. it has among other effects tumoricidal and bacteriocidal effects. NO has for instance cytotoxic effects on human hematological malignant cells from patients with leukemia or lymphoma, whereby NO may be used as a chemotherapeutic agent for treating such hematological disorders, even when the cells have become resistant to conventional anti-cancer drugs.

However, due to the short half-life of NO, it has hitherto been very hard to treat viral, bacteria, virus, fungi or yeast infections with NO. This is because NO is actually toxic in high concentrations and has negative effects when applied in too large amounts to the body. NO is actually also a vasodilator, and too large amounts of NO introduced into the body will cause a complete collapse of the circulatory system. On the other hand, NO has a very short half-life of fractions of a second up to a few seconds, once it is released. Hence, administration limitations due to short half-life and toxicity of NO have been limiting factors in the use of NO in the field of anti-pathogenic and anti-cancerous treatment so far.

In recent years research has been directed to polymers with the capability of releasing nitrogen oxide when getting in contact with water. Such polymers are for example polyalkyleneimines, such as L-PEI (Linear PolyEthyleneImine) and B-PEI (Branched PolyEthyleneImine), which polymers have the advantage of being biocompatible.

U.S. Pat. No. 5,519,020 describes water insoluble polymeric NONOate complexes, such as PEI-C and S-nitrosocompounds, which are capable of accelerating wound repair through the controlled therapeutic release of NO. Clinical applications of the device according to U.S. Pat. No. 5,519, 020 include treatment of burns, burn donor sites, chronic venous ulcers, decubitus ulcers, leprous ulcers, epidermolysis bullosa, scleroderma, psoriasis, and non infected partial thickness wounds. However, the elution of nitric oxide from the polymer according to U.S. Pat. No. 5,519,020 is not regulated in any way. Furthermore, U.S. Pat. No. 5,519,020 is totally silent about the treatment of neuropathy.

Bohl Masters et al. (*Wound Repair Regeneration,* 10((5): 286-294, 2002 XP002335426 US) describes in vitro and in vivo responses to a novel hydrogel, manufactured by ultraviolet light-initiated polymerization from poly(vinyl alcohol) with a NO donor covalently coupled to the polymer backbone, that produces therapeutic levels of NO. (However, the elution is not regulated in any way. Furthermore, this document is totally silent about the treatment of neuropathy.

U.S. Pat. No. 6,737,447 discloses a coating for medical devices, which coating provides NO delivery by using nanofibers of L-PEI. However, the elution of nitric oxide from the polymer according to U.S. Pat. No. 6,737,447 is not regulated in any way. Furthermore, U.S. Pat. No. 6,737,447 is totally silent about the treatment of neuropathy.

EP 1 300 424 discloses extremely hydrophobic NO releasing polymers. These polymers are extensively cross-linked polyamine-derivatized divinylbenzene diazeniumdiolates. However, the elution of nitric oxide from the polymer according to EP 1 300 424 is not regulated in any way. Furthermore, EP 1 300 424 is totally silent about the treatment of neuropathy.

US 2004/0171589 discloses local, differential delivery of nitric oxide within the body. US 2004/0171589 mentions that the device according to US 2004/0171589 may be used for placement on skin wounds or openings, page 2, left column, lines 5 to 6. Furthermore, US 2004/0171589 discloses polyethyleneimine microspheres, with an attached diazeniumdiolate moiety, for long in-situ half-life applications, page 6, right column, lines 1 to 5. However, the elution of nitric oxide from the polymer according to US 2004/0171589 is not regulated in any way. Furthermore, US 2004/0171589 is totally silent about the treatment of neuropathy.

Other example for NO eluting polymers are given in U.S. Pat. No. 5,770,645, wherein polymers derivatized with at least one —$NO_X$ group per 1200 atomic mass unit of the polymer are disclosed, X being one or two. One example is an S-nitrosylated polymer and is prepared by reacting a polythiolated polymer with a nitrosylating agent under conditions suitable for nitrosylating free thiol groups.

Akron University has developed NO-eluting L-PEI molecule that can be nano-spun onto the surface of permanently implanted medical devices such as implanted grafts, showing significant improvement of the healing process and reduced inflammation when implanting such devices. According to U.S. Pat. No. 6,737,447, a coating for medical devices provides nitric oxide delivery using nanofibers of linear poly (ethylenimine)-diazeniumdiolate. Linear poly(ethylenimine) diazeniumdiolate releases nitric oxide (NO) in a controlled manner to tissues and organs to aid the healing process and to prevent injury to tissues at risk of injury.

However, the meaning of "controlled" in the context of U.S. Pat. No. 6,737,447 is only directed to the fact that nitric oxide is eluted from the coating during a period of time. Therefore, the interpretation of "controlled" in respect of U.S. Pat. No. 6,737,447 is different from the meaning of "regulating" in the present invention. "Regulate", according to the present invention is intended to be interpreted as the possibility to vary the elution of nitric oxide to thereby achieve different elution profiles.

Electrospun nanofibers of linear poly(ethylenimine)diazeniumdiolate deliver therapeutic levels of NO to the tissues surrounding a medical device while minimizing the alteration of the properties of the device. A nanofiber coating, because of the small size and large surface area per unit mass of the nanofibers, provides a much larger surface area per unit mass while minimizing changes in other properties of the device.

However, the disclosure is both silent concerning an improvement of present technology in respect of treatment of neuropathy, such as diabetic neuropathy, diabetic ulcers, vaso-constrictive disorders, and enlarged and hardened blood vessels, and the anti pathogenic potential of nitric oxide.

Hence, an improved, or more advantageous, device for therapeutic treatment and/or prevention of neuropathy, such as diabetic neuropathy, diabetic ulcers, and macro-angiopathy is needed. It is desired that said device does increase circulation in the affected area while affecting nerves positively, has a vaso-dilating effect, reduces pain and heals wounds, which device is easy to use, and cost effective, and which device does not develop resistance against the active pharmaceutical substance, and which does not cause local skin or eye irritation, pain etc, and in particular a device allowing for target prevention and treatment of neuropathy, such as diabetic neuropathy, diabetic ulcers, and enlarged and hardened blood vessels, would be advantageous.

SUMMARY OF THE INVENTION

Accordingly, the present invention preferably seeks to mitigate, alleviate or eliminate one or more of the above-identified deficiencies in the art and disadvantages singly or in any combination and solves, among others, the problems mentioned above, by providing a device according to the appended patent claims.

According to one aspect of the invention, a device is provided that allows for target treatment and/or prevention of neuropathy, such as diabetic neuropathy, diabetic ulcers, vaso-constrictive disorders and macro-angiopathy. The device comprises a nitric oxide (NO) eluting polymer arranged to contact the affected area, such that a therapeutic dose of nitric oxide is eluted from said nitric oxide eluting polymer to said area.

According to another aspect of the invention, a manufacturing process for such a device is provided, wherein the process is a process for forming a device that allows for target treatment and/or prevention of neuropathy, such as diabetic neuropathy, diabetic ulcers, and macro-angiopathy. The process comprises selecting a plurality of nitric oxide eluting polymeric fibers, and deploying said nitric oxide eluting fibers in a condom/sheath, patch/dressing or tape/coating to be comprised in said device.

According to still another aspect of the present invention, a use of nitric oxide in a medicament to treat or prevent neuropathy is provided.

The present invention has at least the advantage over the prior art that it provides target exposure of an affected area to NO, whereby an increased circulation in the affected area, a vaso-dilating effect, a positive effect on nerves, pain reduction and wound healing, while not developing resistance against the active pharmaceutical substance, local skin or eye irritation, pain etc, are simultaneously obtained.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION OF THE PREFERRED EMBODIMENTS

The following description focuses on embodiments of the present invention applicable to a device, which allows for simultaneous target treatment and/or prevention of neuropathy, such as diabetic neuropathy, diabetic peripheral neuropathy, or neuropathy and ulcers resulting from said neuropathy as well as a manufacturing method for the latter, and use of nitric oxide.

With regard to nitric oxide (nitrogen monoxide, NO), its physiological and pharmacological roles have attracted much attention and thus have been studied. NO is synthesized from arginine as the substrate by nitric oxide synthase (NOS). NOS is classified into a constitutive enzyme, cNOS, which is present even in the normal state of a living body and an inducible enzyme, iNOS, which is produced in a large amount in response to a certain stimulus. It is known that, as compared with the concentration of NO produced by cNOS, the concentration of NO produced by iNOS is 2 to 3 orders higher, and that iNOS produces an extremely large amount of NO.

In the case of the generation of a large amount of NO as in the case of the production by iNOS, it is known that NO reacts with active oxygen to attack exogenous microorganisms and cancer cells, but also to cause inflammation and tissue injury. On the other hand, in the case of the generation of a small amount of NO as in the case of the production by cNOS, it is considered that NO takes charge of various protective actions for a living body through cyclic GMP (cGMP), such as vasodilator action, improvement of the blood circulation, antiplatelet-aggregating action, antibacterial action, anticancer action, acceleration of the absorption at the digestive tract, renal function regulation, neurotransmitting action, erection (reproduction), learning, appetite, and the like. Heretofore, inhibitors of the enzymatic activity of NOS have been examined for the purpose of preventing inflammation and tissue injury, which are considered to be attributable to NO generated in a large amount in a living body. However, the promotion of the enzymatic activity (or expressed amount) of NOS (in particular, cNOS) has not been examined for the purpose of exhibiting various protective actions for a living body by promoting the enzymatic activity of NOS and producing NO appropriately.

In recent years research has been directed to polymers with the capability of releasing nitrogen oxide when getting in contact with water. Such polymers are for example polyalkyleneimines, such as L-PEI (Linear PolyEthyleneImine) and B-PEI (Branched PolyEthyleneImine), which polymers have the advantage of being biocompatible, after the release of nitrogen oxide.

The polymers employed in embodiments of the present invention may be manufactured by electro spinning, gas spinning, air spinning, wet spinning, dry spinning, melt spinning, and gel spinning. Electro spinning is a process by which a suspended polymer is charged. At a characteristic voltage a fine jet of polymer releases from the surface in response to the tensile forces generated by interaction by an applied electric field with the electrical charge carried by the jet. This process produces a bundle of polymer fibers, such as nanofibers. This jet of polymer fibers may be directed to a surface to be treated.

Furthermore, U.S. Pat. No. 6,382,526, U.S. Pat. No. 6,520,425, and U.S. Pat. No. 6,695,992 disclose processes and apparatuses for the production of such polymeric fibers. These techniques are generally based on gas stream spinning, also known within the fiber forming industry as air spinning, of liquids and/or solutions capable of forming fibers. Gas stream spinning is suited for producing devices according to certain embodiments of the invention.

Figure 1A:
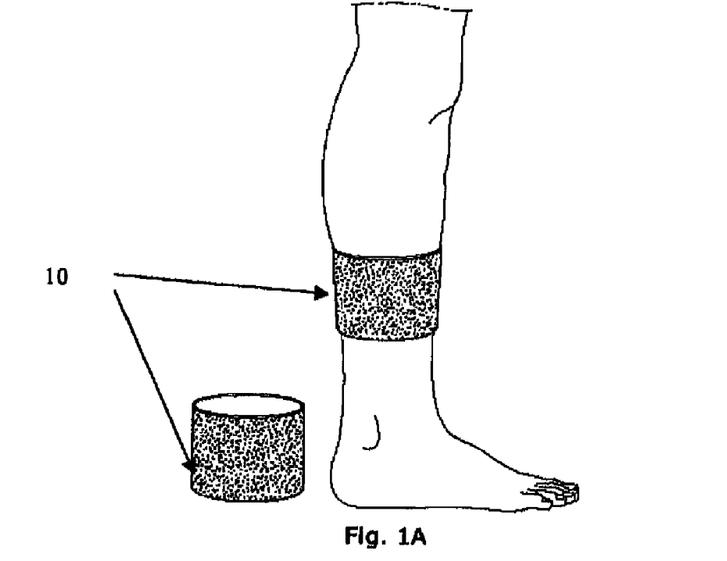
FIG. 1A is a schematic illustration of a treatment device embodiment 10.

FIG. 1A is a schematic illustration of a treatment device embodiment 10. In an embodiment of the invention, according to FIG. 1B, the device is in the form of sock 12, manufactured of a combination of L-PEI or other NO-eluting polymer, such as amino cellulose, amino dextrans, chitosan, aminated chitosan, polyethyleneimine, PEI-cellulose, polypropyleneimine, polybutyleneimine, polyurethane, poly (buthanediol spermate), poly(iminocarbonate), polypeptide, Carboxy Methyl Cellulose (CMC), polystyrene, poly(vinyl chloride), and polydimethylsiloxane, or any combinations of these, and these mentioned polymers grafted to an inert backbone, such as a polysaccharide backbone or cellulosic backbone, and other suitable carrier materials, such as polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly(acrylic acid), Carboxy Methyl Cellulose (CMC), protein based polymers, gelatine, biodegradable polymers, cotton, and latex, or any combinations of these, as base material, said sock being expandable, where NO is allowed to be eluted, said sock being covered on the inside with nanofilament of NO-eluting L-PEI. The base material of the sock may also be cotton, polyacrylate or any other fabric used in the clothing industry, in which cases the base material is loaded with the NO-eluting polymer according to the invention. This embodiment provides an easy to use sock, which is applied on the affected area in the same way as normal clothing. In another embodiment of the present invention the sock is covered on the inside with nanofilament of any other suitable polymer, according to above. Such polymers are for example other polyalkyleneimines, such as B-PEI (Branched PolyEthylenelmine), which polymers have the advantage of being biocompatible, after the release of nitrogen oxide.

Other example for NO eluting polymers are given in U.S. Pat. No. 5,770,645, wherein polymers derivatized with at least one —NOX group per 1200 atomic mass unit of the polymer are disclosed, X being one or two. One example is an S-nitrosylated polymer and is prepared by reacting a polythiolated polymer with a nitrosylating agent under conditions suitable for nitrosylating free thiol groups.

Akron University has developed NO-eluting L-PEI molecule that can be nano-spun onto the surface of permanently implanted medical devices such as implanted grafts, showing significant improvement of the healing process and reduced inflammation when implanting such devices. According to U.S. Pat. No. 6,737,447, a coating for medical devices provides nitric oxide delivery using nanofibers of linear poly (ethylenimine)-diazeniumdiolate. Linear poly(ethylenimine) diazeniumdiolate releases nitric oxide (NO) in a controlled manner.

However, the meaning of "controlled" in the context of U.S. Pat. No. 6,737,447 is only directed to the fact that nitric oxide is eluted from the coating during a period of time, i.e. that the nitric oxide is not eluted all at once. Therefore, the interpretation of "controlled" in respect of U.S. Pat. No. 6,737,447 is different from the meaning of "regulating" in the present invention. "Regulate or control", according to the present invention is intended to be interpreted as the possibility to vary the elution of nitric oxide to thereby achieve different elution profiles.

A polymer comprising an O-nitrosylated group is also a possible nitric oxide eluting polymer. Thus, in one embodiment of the present invention, the nitric oxide eluting polymer comprises diazeniumdiolate groups, S-nitrosylated and O-nitrosylated groups, or any combinations thereof.

In still another embodiment of the present invention said nitric oxide eluting polymer is a poly(alkyleneimine)diazeniumdiolate, such as L-PEI-NO (linear poly(ethyleneimine) diazeniumdiolate), where said nitric oxide eluting polymer is loaded with nitric oxide through the diazeniumdiolate groups and arranged to release nitric oxide at a treatment site.

Some other examples of a suitable nitric oxide eluting polymer are selected from the group comprising mino cellulose, amino dextrans, chitosan, aminated chitosan, polyethyleneimine, PEI-cellulose, polypropyleneimine, polybutyleneimine, polyurethane, poly(buthanediol spermate), poly (iminocarbonate), polypeptide, Carboxy Methyl Cellulose (CMC), polystyrene, poly(vinyl chloride), and polydimethylsiloxane, or any combinations of these, and these mentioned polymers grafted to an inert backbone, such as a polysaccharide backbone or cellulosic backbone.

In still another embodiment of the present invention the nitric oxide eluting polymer may be a O-derivatized NON-Oate. This kind of polymer often needs an enzymatic reaction to release nitric oxide.

Other ways of describing polymers, which may be suitable as nitric oxide eluting polymer, is polymers comprising secondary amine groups (=N—H), such as L-PEI, or have a secondary amine (=N—H) as a pendant, such as aminocellulose.

Figure 1B:
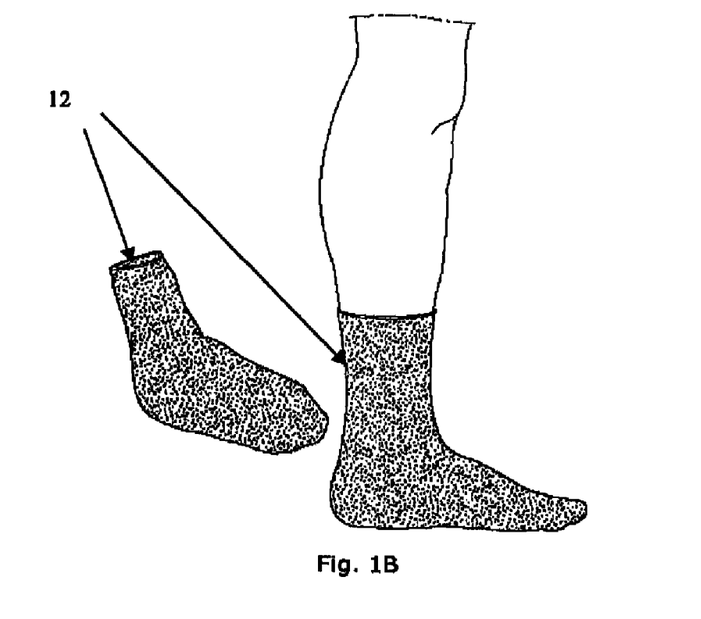
FIG. 1B is a schematic illustration of a sock 12 according to an embodiment of the invention.

It is most preferable that the nano-spun fibers in the NO-eluting sock according to the present embodiment of the present invention comprise L-PEI. Also, nitric oxide eluting fibers to be woven into the sock are suitably produced from L-PEI and loaded with NO for release thereof at use.

The term "nano-spun fibers" is in the context of the present invention intended to be interpreted as fibers obtained by all processes producing fibers of nano-size, such as electro spinning, air spinning, wet spinning, dry spinning, melt spinning, gel spinning.

This sock may be in any suitable size, such as a suitable size for covering any body part to be treated, such as a foot or individual toes, a calf, a thigh, the whole or a part of an abdomen, a neck, the whole or a part of a head, a shoulder, an upper arm, a forearm, a hand or individual fingers. These sizes may for example vary from small, medium, and large sized socks, depending on the size of the person to be treated.

When the NO-eluting sock 12 according to the present embodiment of the invention is applied on the area to be treated, according to FIG. 1B, and gets in contact with the moisture, in the form of secreted sweat, or sprayed proton donor, the NO-eluting sock starts to release NO to the area to be treated.

In another embodiment of the present invention the sock is covered on the inside with NO-eluting nanoparticles, or microspheres. These nanoparticles, or microspheres, may be formed from the NO-eluting polymers, encapsulated in any suitable material, such as polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly(acrylic acid), Carboxy Methyl Cellulose (CMC), protein based polymers, gelatine, biodegradable polymers, cotton, and latex, or any combinations of these. When the nanoparticles, or microspheres, according to this embodiment, gets in contact with the secreted moisture, in form of sweat, or sprayed proton donor, on the inside of the sock, they start to elute NO on the area to be treated.

In the context of the present invention the term "encapsulating" is intended to be interpreted as fixating the nitric oxide eluting polymer in a three dimensional matrix such as a foam, a film, a nonwoven mat of nanofibers, fibers, or other materials with the capability to fixate the NO eluting polymer, or enclosing the nitric oxide eluting polymer in any suitable material.

In yet another embodiment of the present invention the sock contains a small water bag or sealed water sponge. This water bag or sealed water sponge is used to activate the elution of NO from the NO-eluting polymer, nanoparticles, and/or microspheres. Persons that do not easily sweat may be helped by the use of this embodiment.

In another embodiment of the present invention a nitric oxide eluting polymer is provided, and/or combined, with microencapsulated proton donor.

This may for example be done by first manufacturing microcapsules, containing a proton donor, such as water or water containing liquid, in a state of the art manner. These microcapsules are then applied on the NO eluting polymer. The application of the microcapsules on the NO eluting polymer may for example be done by gluing, such as pattern gluing, or instead spinning the NO eluting polymer onto said microcapsules. In this way a device or a system, comprising NO eluting polymer and microencapsulated proton donor is manufactured. When the device or system is applied on the target area the device or system is compressed or squeezed. Said compression or squeezing results in breakage of the microcapsules. The NO eluting polymer is thus exposed to proton donor, and the elution of NO from the NO eluting polymer is initiated on the target area. In other embodiments of the present invention the proton donor inside the microcapsules is released by heating or shearing the microcapsules until the microcapsules are ruptured.

In still another embodiment the microcapsules are formed into a film, tape, or sheath. Thereafter, a film, tape, or sheath of an NO eluting polymer is glued onto the film, tape, or sheath of microcapsules. Preferably the film, tape, or sheath of the NO eluting polymer is glued onto the film, tape, or sheath of the microcapsules in a patterned way. The obtained pattern includes spaces where there is no glue, in which spaces the proton donor will be transported to the NO eluting polymer once the microcapsules are broken from compression or squeezing. When the proton donor gets in contact with the NO eluting polymer the elution of NO starts. Thus, the combination of film, tape, or sheath of microcapsules and NO eluting polymer may be applied on a target area. Thereafter the combination is compressed or squeezed, which results in that the target area is exposed to NO.

In yet another embodiment the NO eluting polymer is spun directly onto the film, tape, or sheath of microcapsules, containing proton donor. The combination of film, tape, or sheath of microcapsules and spun NO eluting polymer may be applied on a target area. Thereafter the combination is compressed or squeezed, which results in that the target area is exposed to NO.

In still another embodiment of the present invention the device or system is provided with an activation indicator. This activation indicator indicates when the microcapsules are satisfyingly broken, hence when the NO eluting polymer is subjected to enough proton donor to elute an efficient amount of NO. This activation indicator may for example be obtained by coloring the proton donor that is trapped inside the microcapsules. When the microcapsules are broken the colored proton donor escapes the microcapsules and the color gets visualized while efficiently wetting the NO eluting polymer. Another way of obtaining an activation indicator is to choose to manufacture the microcapsules in a material, or choose a wall thickness of said microparticles, that creates a sound when the microcapsules break. It is also possible to admix a scent in the proton donor, contained in the microcapsules. This results in that the user of the device or system may smell the scent when the proton donor escapes from the microcapsules after breakage thereof.

In another embodiment a substance that changes color when it comes in contact with water can be incorporated in the device. Thus when the water capsules or water bag breaks the material changes color, thereby indicating that the material is activated.

In another embodiment of the present invention the device or system only allows NO-elution in one direction. In this kind of embodiment one side of the device has low permeability, or substantially no permeability, to nitric oxide. This may also be accomplished by applying a material on one side of the device according to the invention that is not permeable to NO. Such materials may be chosen from the group comprising common plastics, such as fluoropolymers, polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly(acrylic acid), Carboxy Methyl Cellulose (CMC), protein based polymers, gelatine, biodegradable polymers, cotton, and latex, or any combinations of these. This embodiment is also easy to manufacture as the NO eluting polymer, e.g. L-PEI (or nitric oxide eluting polymer and carrier material, which will be explained in more detail below) may be electro or gas-et spun onto the surface of the device according to the invention of e.g. the mentioned plastics, latex, or cotton.

In still another embodiment the device is provided with one membrane, which is permeable to nitric oxide, on a first side of the device, and another membrane, which has low permeability or substantially no permeability to nitric oxide, on a second side of said device. This embodiment provides the possibility to direct the elution to said first side of the device, while the elution of nitric oxide is substantially prevented from said second side. Thereby, a greater amount of nitric oxide will reach the intended area to be treated.

The activation of the nitric oxide eluting polymer may be accomplished by contacting said polymer with a suitable proton donor. In one embodiment the proton donor may be selected from the group comprising water, body fluids (blood, lymph, bile, etc.), alcohols (methanol, ethanol, propanols, buthanols, pentanols, hexanols, phenols, naphtols, polyols, etc.), aqueous acidic buffers (phosphates, succinates, carbonates, acetates, formats, propionates, butyrates, fatty acids, amino acids, etc.), or any combinations of these.

By adding a surfactant in the proton donor one can facilitate the wetting of the device. The surfactant lowers the surface tension and the activating fluid is easily transported throughout the device.

Figure 2:
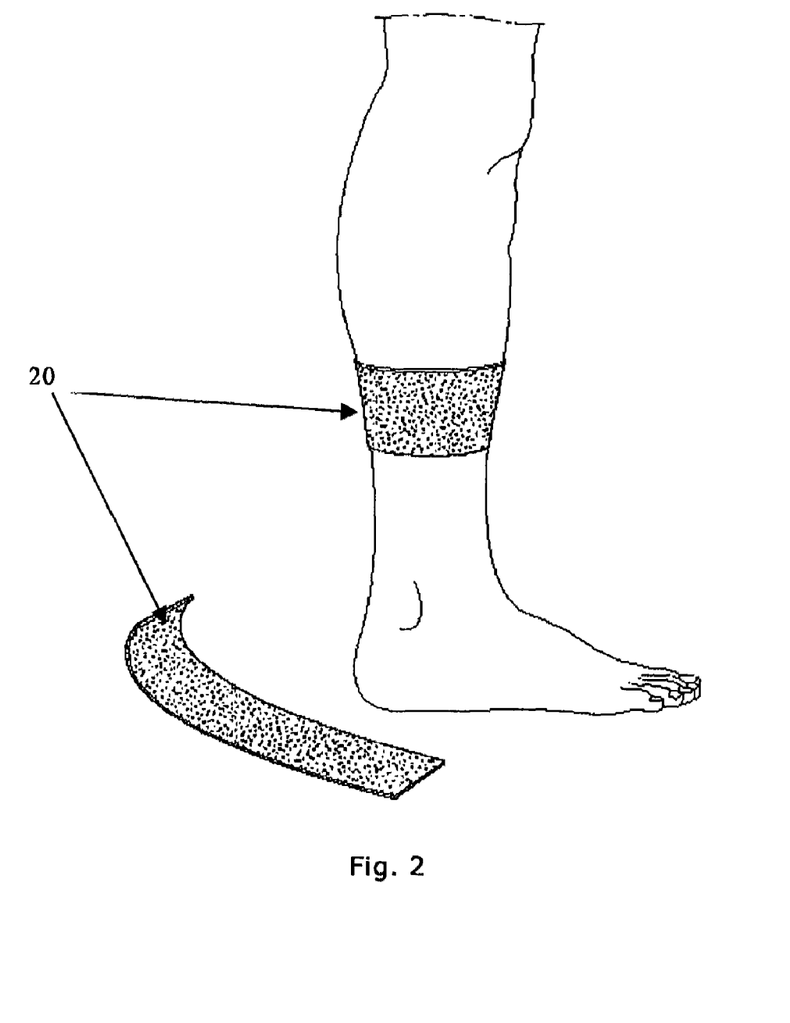
FIG. 2 is a schematic illustration of a tape or coating 20 according to another embodiment of the invention.

In still another embodiment of the device according to the present invention, it may be manufactured in the form of a polyurethane, or polyethylene, tape or coating, according to FIG. 2. This polyurethane tape or coating may easily be wrapped around the body part to be treated. At least the side facing the body part may be covered with NO-eluting nanoparticles, microspheres, or nanofilament of NO-eluting L-PEI. When these particles or filaments get in contact with the moisture, in form of sweat, on the inside of the tape or coating, the elution of NO starts.

This embodiment makes it possible to obtain a device that may be applied on locations that are difficult to get at with a sock, such as in between the toes or fingers, the groin, the armpit etc.

In other embodiments of the invention, the tape or coating may be manufactured by any other suitable material, such as rubbers and polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly(acrylic acid), Carboxy Methyl Cellulose (CMC), protein based polymers, gelatine, biodegradable polymers, cotton, and latex, or any combinations of these.

In another embodiment these nanoparticles, or microspheres, may be integrated in a soluble film that disintegrates on the inside of the sock or tape/coating, in order to elute NO at the area of interest when the soluble film gets in contact with the moisture, in form of sweat or from the water bag or sealed water sponge, or spraying water on the area to be treated.

When placed on an area to be treated the device provides target treatment and/or prevention of neuropathy, such as diabetic neuropathy, diabetic ulcers, and macro-angiopathy.

In another embodiment of the present invention the device only allows NO-elution in one direction. In this kind of embodiment one side of the sock or tape/coating is non-permeable to NO. This may be accomplished by applying a material on one side of the sock or tape/coating that is not permeable to NO. Such materials may be chosen from the group comprising common plastics, such as polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly(acrylic acid), Carboxy Methyl Cellulose (CMC), protein based polymers, gelatine, biodegradable polymers, cotton, and latex, or any combinations of these.

Figure 3:
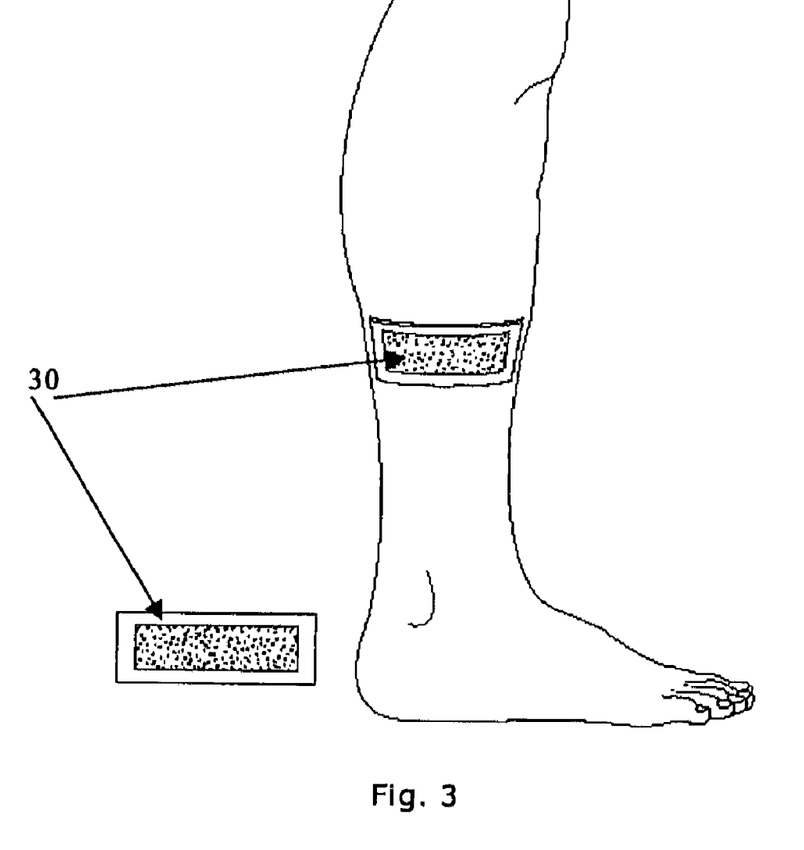
FIG. 3 is a schematic illustration of a sheath or plaster 30 according to a further embodiment of the invention.

In another embodiment of the present invention, the device is in the form of polyurethane or polyethylene sheaths or plasters, pads or dressings according to FIG. 3, coated with the NO-eluting polymer. The plaster or sheath may be applied on the area to be treated with the aid of an adhering material, such as glue etc. This embodiment has the advantage of being applicable on smaller areas or wounds, when there is no need, or if the person to be treated finds it unpleasant, to cover the whole body part with a sock or coating/tape. It is also an advantage that the device in form of a plaster or sheath or pad or dressing needs lesser amount of material, thus lower manufacturing cost.

The devices according to the embodiments may also be covered with a powder manufactured from nanofibers of NO-eluting polymer, such as L-PEI.

In yet another embodiment of the present invention the NO-eluting device is acting as a booster for drug eluting patches, e.g. pharmaceuticals, vitamins, nicotin, nitroglycerin etc. This embodiment presents a device with the advantage of combining two therapeutic treatments, of significant value, in one treatment. Hence, a synergetic effect may be achieved by such devices when NO is eluted from the device. NO has a vasodilatory effect on the region where the device having the combination compound actuates. Vasodilated tissue is more susceptible to certain medications and thus more easily treated by the medical preparations and still NO has in addition to that the anti-inflammatory, anti-bacterial etc. effect. Hence, an unexpected surprisingly effective treatment is provided.

In another embodiment of the device according to the present invention the fibers, nanoparticles, or microspheres may be integrated in a gel, that may either be in a smearing or compressed structure. The elution of NO may then be initiated by applying a water soaked patch on said gel. The fibers, nanoparticles, or microspheres may also be integrated in a hydrogel, which is mixed directly before use. This embodiment has the advantage of being able to penetrate pockets and corners in the skin for closer elution of NO on the area to be treated.

In still another embodiment the nitric oxide eluting polymer, such as powder, nanoparticles or microspheres, can be incorporated in foam. The foam may have an open cell structure, which facilitates the transport of the proton donor to the nitric oxide eluting polymer. The foam can be of any suitable polymer such as polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly(acrylic acid), Carboxy Methyl Cellulose (CMC), protein based polymers, gelatine, biodegradable polymers, cotton, polyolefins, and latex, or any combinations of these, or latex.

In another embodiment the device is in the form of a cream, a gel or a combination of the two. Since the nitric oxide eluting polymer is activated by proton donors the nitric oxide eluting polymer has to be separate from the proton donor until one wants to initiate the elution of nitric oxide, i.e. use the device. One way to accomplish this is to have a syringe with two separate containers. In one container you have a proton donor-based gel and in the other a non proton donor-based gel, comprising the nitric oxide eluting polymer. Upon using the device the two gels are squeezed from the syringe and mixed together, the proton donor in the first gel comes in contact with the nitric oxide eluting polymer in the second gel and the elution of nitric oxide starts.

The device elutes nitric oxide (NO) from said eluting polymer in a therapeutic dose, such as between 0.001 to 5000 ppm, such as 0.01 to 3000 ppm, such as 0.1 to 1000 ppm, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 91, 92, 93, 94, 95, 96, 97, 98, 99, or 100 ppm. The concentration may vary widely depending on where the concentration is measured. If the concentration is measured close to the actual NO eluting polymer the concentration may be as high as thousands of ppm, while the concentration inside the tissue in this case often is considerably lower, such as between 1 to 1000 ppm.

In the embodiments of the present invention it may be suitable to control or regulate the time span of NO release from the device according to the invention. This may be accomplished by integrating other polymers or materials in said device. These polymers or materials may be chosen from any suitable material or polymer, such as polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly(acrylic acid), Carboxy Methyl Cellulose (CMC), protein based polymers, gelatine, biodegradable polymers, cotton, polyolefins, and latex, or any combination of these.

Three important factors in controlling and regulating the elution of nitric oxide from a nitric oxide eluting polymer are how quickly a proton donor comes in contact with the nitric oxide releasing polymer, such as a diazoliumdiolate group, the acidity of the environment surrounding the nitric oxide eluting polymer, and the temperature of the environment surrounding the nitric oxide releasing polymer (higher temperature promotes elution of nitric oxide).

Figure 4:
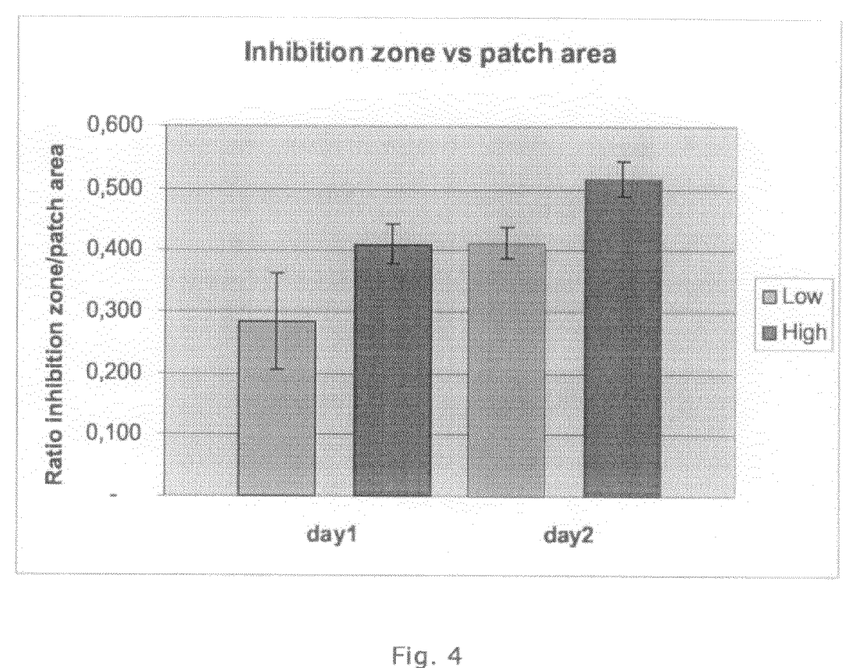
FIG. 4 is a graph illustrating different elutions of nitric oxide from two polymer mixtures. The elution profile (NO concentration vs. time) for L-PEI-NO mixed with a hydrophilic carrier polymer (polyethylene oxide) in an acidic environment represented by the darker bars, and the elution profile (NO concentration vs. time) for a L-PEI-NO mixed with a hydrophobic carrier polymer (polystyrene) in a neutral environment is represented by the lighter bars.

In one embodiment of the present invention a nitric oxide eluting polymer, such as L-PEI-NO, is mixed with a carrier polymer to slow down or prolong the elution of nitric oxide. Also, in another embodiment, the nitric oxide eluting polymer may be mixed with more than one carrier polymer, whereby be elution or release may be tailor made to fit specific needs. Such a need may for example be a low elution during a first period of time, when the environment of the nitric oxide eluting polymer is hydrophobic, and a faster elution during a second period of time, when the environment of the nitric oxide eluting polymer has been altered to be more hydrophilic. This may for example be accomplished by using biodegradable polymers, whereby a low elution during a first period of time is obtained, after which, when the hydrophobic polymer has been dissolved, the hydrophilic polymer provides a higher elution of nitric oxide. Thus, a more hydrophobic carrier polymer will give a slower elution of nitric oxide, since the activating proton donor, such as water or body fluid, will penetrate the carrier polymer slower. On the other hand, a hydrophilic polymer acts the opposite way. One example of an hydrophilic polymer is polyethylene oxide, and one example of an hydrophobic polymer is polystyrene. These carrier polymers may be mixed with the nitric oxide eluting polymer and then electrospun to suitable fibers. The skilled person in the art knows which other polymers may be used for similar purposes. FIG. 4 illustrates two elution profiles (NO concentration vs. time) for two different polymer mixtures; a nitric oxide eluting polymer mixed with a hydrophilic carrier polymer in an acidic environment labeled as "high" in the figure, and a nitric oxide eluting polymer mixed with a hydrophobic carrier polymer in a neutral environment labeled as "low" in the figure.

In one embodiment this carrier polymer is substituted by another material with hydrophobic or hydrophilic properties. Therefore, the term "carrier material" in the present context should be interpreted to include carrier polymers and other materials with hydrophilic or hydrophobic properties.

In another embodiment of the present invention the elution of nitric oxide from a nitric oxide eluting polymer, such as L-PEI-NO, is influenced by the presence of protons. This means that a more acidic environment provides a quicker elution of nitric oxide. By activating the nitric oxide eluting polymer, or mixture of nitric oxide eluting polymer and carrier material, with an acidic fluid, such as an ascorbic acid solution, the elution of nitric oxide may be accelerated.

The carrier polymers and carrier materials mentioned above may affect other characteristics than the regulation of nitric oxide elution. An example of such characteristic is mechanical strength.

In respect of the carrier polymers or carrier materials, the NO-eluting polymer may be integrated in, spun together with, or spun on top of, any of these materials in all of the embodiments of the present invention. This spinning includes electro spinning, air spinning, dry spinning, wet spinning, melt spinning, and gel spinning. In this way, one may manufacture fibers of a polymer mixture, comprising a nitric oxide eluting polymer and a carrier polymer, or a carrier material, with predefined nitric oxide eluting characteristics. These characteristics may be tailor made for different elution profiles in different applications.

The NO-eluting polymers in the devices may be combined with silver, such as hydroactivated silver. The integration of silver in the devices gives the healing process an extra boost. Preferably the silver is releasable from the devices in the form of silver ions. The integration of silver in the device may present several advantages. One example of such an advantage is that the silver may keep the device in itself free from bacteria or viruses, while the nitric oxide eluting polymer elutes the therapeutic dosage of nitric oxide to the target site.

The device may be manufactured by, for example electro spinning of L-PEI. L-PEI is the charged at a characteristic voltage, and a fine jet of L-PEI releases as a bundle of L-PEI polymer fibers. This jet of polymer fibers may be directed to a surface to be treated. The surface to be treated may for example be any suitable material in respect of a device. The electro spun fibers of L-PEI then attach on said material and form a coating/layer of L-PEI on the device according to the invention.

The basic material of the device may be polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly (acrylic acid), Carboxy Methyl Cellulose (CMC), protein based polymers, gelatine, biodegradable polymers, cotton, polyolefins, and latex, or any combinations of these, or latex. The NO-eluting polymer may be integrated in, spun together with, or spun on top of, any of these materials in all of the embodiments of the present invention.

The nitric oxide eluting polymer may comprise a secondary amine, either in the backbone or as a pendant, as described previously. This will make a good nitric oxide eluting polymer. The secondary amine should have a strong negative charge to be easy to load with nitric oxide. If there is a ligand close to the secondary amine, such as on a neighbor carbon atom to the nitrogen atom, with higher electronegativity than nitrogen (N), it is very difficult to load the polymer with nitric oxide. On the other hand, if there is a positive ligand close to the secondary amine, such as on a neighbor carbon atom to the nitrogen atom, the electronegativity of the amine will increase and thereby increase the possibility to load the nitric oxide elution polymer with nitric oxide.

In an embodiment of the present invention the nitric oxide polymer may be stabilized with a salt. Since the nitric oxide eluting group, such as a diazeniumdiolate group, is negative, a positive counter ion, such as a cation, may be used to stabilize the nitric oxide eluting group. This cation may for example be selected from the group comprising any cation from group 1 or group 2 in the periodic table, such as $Na^+$, $K^+$, $Li^+$, $Be^{2+}$, $Ca^{2+}$, $Mg^{2+}$, $Ba^{2+}$, and/or $Sr^{2+}$. Different salts of the same nitric oxide eluting polymer have different properties. In this way a suitable salt (or cation) may be selected for different purposes. Examples of cationic stabilized polymers are L-PEI-NO—Na, i.e. L-PEI diazeniumdiolate stabilized with sodium, and L-PEI-NO—Ca, i.e. L-PEI diazeniumdiolate stabilized with calcium.

Another embodiment of the present invention comprises mixing the nitric oxide eluting polymer, or a mixture of the nitric oxide eluting polymer and a carrier material, with an absorbent agent. This embodiment provides the advantage of an accelerated elution of nitric oxide since the polymer, or polymer mixture, via the absorbent agent, may take up the activating fluid, such as water or body fluid, much faster. In one example 80% (w/w) absorbent agent is mixed with the nitric oxide eluting polymer, or mixture of nitric oxide eluting polymer and carrier material, and in another embodiment 10 to 50% (w/w) absorbent agent is mixed with the nitric oxide eluting polymer, or mixture of nitric oxide eluting polymer and carrier material.

Since the elution of nitric oxide is activated by a proton donor, such as water, it may be an advantage to keep the nitric oxide eluting polymer, or mixture of nitric oxide eluting polymer and carrier material, in contact with said proton donor. If an indication requires an elution of nitric oxide during a prolonged period of time, a system is advantageous, which presents the possibility to keep the proton donor in contact with the nitric oxide eluting polymer, or mixture of nitric oxide eluting polymer and carrier material. Therefore, in still another embodiment of the present invention, the elution of nitric oxide may be regulated by adding an absorbent agent. The absorbent agent absorbs the proton donor, such as water, and keeps the proton donor in close contact with the nitric oxide eluting polymer during prolonged periods of time. Said absorbent agent may be selected from the group comprising polyacrylates, polyethylene oxide, carboxymethylcellulose, and microcrystalline cellulose, cotton, and starch. This absorbent agent may also be used as a filling agent. In this case said filling agent may give the nitric oxide eluting polymer, or mixture of said nitric oxide eluting polymer and a carrier material, a desired texture.

It is of course possible to electro spin the other NO-eluting polymers, according to above, on the device according to the invention while still being inside the scope of the present invention.

In one embodiment the NO-eluting polymers employed in the devices according to the present invention are electro spun in such way that pure NO-eluting polymer fibers may be obtained.

Gas stream spinning, air spinning, wet spinning, dry spinning, melt spinning, or gel spinning of said NO-eluting polymers onto the device is also within the scope of the present invention.

The manufacturing process presents the advantages of large contact surface of the NO-eluting polymer fibers or microparticles with the area to be treated, effective use of NO-eluting polymer, and a cost effective way of producing the device.

Hereinafter, some potential uses of the present invention are described:

A method of therapeutically treating and/or preventing neuropathy and ulcers at a treatment side of a body, by means of a device that comprises a nitric oxide (NO) eluting polymer configured for eluting a therapeutic dosage of nitrogen oxide (NO) when used for said treatment, comprising exposing said treatment site of said infection in or on a body to said nitric oxide when said polymer in use elutes nitrogen oxide (NO) by eluting a therapeutic dose of nitric oxide from said nitric oxide eluting polymer to said treatment site.

The method according to the above, wherein said site is an extremity of a body, and wherein said method comprises applying a condom/sheath, sock, patch/pad/dressing, and tape/coating to said extremity for said exposure.

Use of nitric oxide (NO) in a therapeutic dose for therapeutically treating and/or preventing neuropathy and ulcers at a treatment side of a body.

The invention may be implemented in any suitable form. The elements and components of the embodiments according to the invention may be physically, functionally, and logically implemented in any suitable way. Indeed, the functionality may be implemented in a single unit, in a plurality of units, or as part of other functional units.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented. Additionally, although individual features may be included in different claims, these may possibly advantageously be combines, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

What is claimed is:

1. A non-implantable device for treating neuropathy, or neuropathy and ulcers resulting from said neuropathy, at a target site of a body, wherein said device comprises:
   a nitric oxide (NO) eluting polymer configured to elute a therapeutic dosage of nitric oxide (NO) when contacted with a proton donor, at said target site on a body;
   a carrier material; and
   a proton donor container, a proton donor bag, a sealed proton donor sponge, or a microencapsulated proton donor.

2. The device according to claim 1, wherein said device is configured to direct eluted nitric oxide substantially towards said target site.

3. The device according to claim 2, further comprising a first membrane which is permeable to nitric oxide on a first side of the device, wherein said first side is oriented towards said treatment site, and a second membrane which has low permeability or substantially no permeability to nitric oxide on a second side of said device, wherein said second side is oriented away from said treatment site, wherein said substantial direction of nitric oxide (NO) from said device is provided as the elution of nitric oxide from said device and is substantially prevented from said second side.

4. The device according to claim 1, wherein said nitric oxide (NO) eluting polymer comprises diazeniumdiolate groups, S-nitrosylated groups, O-nitrosylated groups, or any combination thereof.

5. The device according to claim 4, wherein said nitric oxide (NO) eluting polymer is L-PEI (linear polyethyleneimine).

6. The device according to claim 4, wherein said nitric oxide eluting polymer is selected from the group consisting of amino cellulose, amino dextrans, chitosan, aminated chitosan, polyethyleneimine, PEI-cellulose, polypropyleneimine, polybutyleneimine, polyurethane, poly(buthanediol spermate), poly(iminocarbonate), polypeptide, Carboxy Methyl Cellulose (CMC), polystyrene, poly(vinyl chloride), polydimethylsiloxane, and any combination thereof, wherein said polymer is grafted to an inert backbone selected from the group consisting of a polysaccharide backbone and a cellulosic backbone.

7. The device according to claim 1, wherein said device is selected from the group consisting of a sock, a tape/coating, a patch/dressing and a plaster.

8. The device according to claim 7, wherein said sock, tape/coating, or plaster is manufactured from polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly (acrylic acid), Carboxy Methyl Cellulose (CMC), protein based polymers, gelatine, biodegradable polymers, cotton, polyolefins, latex, or any combination thereof.

9. The device according to claim 1, wherein said device is partly disintegrable when subjected to a proton donor.

10. The device according to claim 9, wherein said proton donor is selected from the group consisting of water, methanol, ethanol, propanols, butanols, pentanols, hexanols, phenols, naphthols, polyols, phosphates, succinates, carbonates, acetates, formates, propionates, butyrates, fatty acids, amino acids, and any combination thereof.

11. The device according to claim 10, wherein said proton donor comprises a surfactant for facilitating wetting of the device.

12. The device according to claim 1, wherein said polymer comprises silver.

13. The device according to claim 1, wherein said nitric oxide eluting polymer is in form of nanoparticles or microspheres.

14. The device according to claim 13, wherein said nanoparticles or microspheres are encapsulated in a material selected from the group consisting of polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly(acrylic acid), Carboxy Methyl Cellulose (CMC), protein based polymers, gelatine, biodegradable polymers, cotton, polyolefins, latex, and any combination thereof.

15. The device according to claim 13, wherein said nanoparticles or microspheres are integrated in a gel, hydrogel, foam or cream.

16. The device according to claim 1, wherein said carrier material is selected from the group consisting of polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly (acrylic acid), Carboxy Methyl Cellulose (CMC), protein based polymers, gelatine, biodegradable polymers, cotton, polyolefins, latex and any combination thereof.

17. The device according to claim 1, wherein said nitric oxide eluting polymer comprises a secondary amine in the backbone or a secondary pendant amine.

18. The device according to claim 17, wherein a positive ligand is located on a neighbor atom to the secondary amine.

19. The device according to claim 1, further comprising an absorbent agent.

20. The device according to claim 19, wherein said absorbent agent is selected from the group consisting of polyacrylate, polyethylene oxide, Carboxy Methyl Cellulose (CMC), microcrystalline cellulose, cotton, starch, and any combination thereof.

21. The device according to claim 1, further comprising a cation, wherein said cation stabilizes the nitric oxide eluting polymer.

22. The device according to claim 21, wherein said cation is selected from the group consisting of Na+, K+, Li+, Be2+, Ca2+, Mg2+, Ba2+, Sr2+, and any combination thereof.

23. The device according to claim 1, wherein said carrier material is a hydrogel.

24. The device according to claim 1, wherein the device is a syringe-type device having two separate containers, wherein a first container contains a proton donor-based NO release activation agent, and a second container contains a non proton donor-based gel comprising the nitric oxide eluting polymer, wherein the syringe-type device is configured to provide admixing upon administration to said target site.

25. A device for the treatment of neuropathy, or neuropathy and ulcers resulting from said neuropathy, said device comprising a nitric oxide (NO) eluting polymer and a sealed enclosure containing a proton donor, wherein nitric oxide is eluted from said device as nitric oxide (NO) from said NO eluting polymer in a therapeutic dose when said sealed enclosure containing a proton donor is opened and said proton donor contacts said NO eluting polymer at a target site of a body.

26. The device according to claim 25, wherein said therapeutic dose is 0.001 to 5000 ppm.

27. A device for the treatment of neuropathy, or neuropathy and ulcers resulting from said neuropathy, said device comprising:
a proton donor enclosed in a breakable sealed storage enclosure and a nitric oxide (NO) eluting polymer configured to elute a therapeutic dosage of nitric oxide (NO) when contacted with a proton donor wherein:
said nitric oxide (NO) eluting polymer is located between a first membrane that is permeable to nitric oxide and a second membrane that is substantially impermeable to nitric oxide and
said device is configured to be placed on a target treatment site to deliver nitric oxide (NO) through said first membrane substantially in a direction towards the target treatment site when said breakable sealed storage enclosure containing said proton donor is broken.

* * * * *